United States Patent
Boss et al.

(10) Patent No.: US 9,914,721 B2
(45) Date of Patent: Mar. 13, 2018

(54) USE OF BENZIMIDAZOLE-PROLINE DERIVATIVES

(71) Applicant: IDORSIA PHARMACEUTICALS LTD, Allschwil (CH)

(72) Inventors: Christoph Boss, Allschwil (CH); Catherine Roch, Allschwil (CH); Christine Brotschi, Allschwil (CH); Markus Gude, Allschwil (CH); Bibia Heidmann, Allschwil (CH); Francois Jenck, Allschwil (CH); Thierry Sifferlen, Allschwil (CH); Michel Steiner, Allschwil (CH); Jodi T. Williams, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/101,871

(22) PCT Filed: Dec. 3, 2014

(86) PCT No.: PCT/IB2014/066548
§ 371 (c)(1),
(2) Date: Jun. 3, 2016

(87) PCT Pub. No.: WO2015/083094
PCT Pub. Date: Jun. 11, 2015

(65) Prior Publication Data
US 2017/0001985 A1    Jan. 5, 2017

(30) Foreign Application Priority Data

Dec. 4, 2013  (WO) ................. PCT/IB2013/060630

(51) Int. Cl.
*A61K 31/4184* (2006.01)
*C07D 403/14* (2006.01)
*A61K 31/4178* (2006.01)
*A61K 31/4192* (2006.01)
*A61K 31/506* (2006.01)

(52) U.S. Cl.
CPC ........ *C07D 403/14* (2013.01); *A61K 31/4178* (2013.01); *A61K 31/4192* (2013.01); *A61K 31/506* (2013.01)

(58) Field of Classification Search
CPC ............ A61K 31/4178; A61K 31/4192; A61K 31/506; C07D 403/14
USPC .................................. 514/394, 256
See application file for complete search history.

(56) References Cited

U.S. PATENT DOCUMENTS

| | | | |
|---|---|---|---|
| 3,282,927 A | 11/1966 | Alfred et al. | |
| 6,660,759 B1 | 12/2003 | Hattori et al. | |
| 7,105,538 B2 | 9/2006 | Hennies et al. | |
| 7,763,638 B2 | 7/2010 | Aissaoui et al. | |
| 7,994,336 B2 | 8/2011 | Aissaoui et al. | |
| 8,063,099 B2 | 11/2011 | Aissaoui et al. | |
| 8,106,215 B2 | 1/2012 | Aissaoui et al. | |
| 8,133,901 B2 | 3/2012 | Aissaoui et al. | |
| 8,236,801 B2 | 8/2012 | Aissaoui et al. | |
| 8,236,964 B2 | 8/2012 | Aissaoui et al. | |
| 8,288,411 B2 | 10/2012 | Aissaoui et al. | |
| 8,288,429 B2 | 10/2012 | Aissaoui et al. | |
| 8,288,435 B2 | 10/2012 | Aissaoui et al. | |
| 8,895,606 B2 | 11/2014 | Boss et al. | |
| 9,000,029 B2 | 4/2015 | Boss et al. | |
| 9,150,566 B2 | 10/2015 | Bolli et al. | |
| 9,211,279 B2 | 12/2015 | Boss et al. | |
| 9,242,970 B2 | 1/2016 | Aissaoui et al. | |
| 9,303,023 B2 | 4/2016 | Bolli et al. | |
| 2003/0055037 A1 | 3/2003 | Delombaert et al. | |
| 2005/0014765 A1 | 1/2005 | Mailliet et al. | |
| 2006/0019975 A1 | 1/2006 | Humphrey et al. | |
| 2009/0082394 A1 | 3/2009 | Jenck et al. | |
| 2010/0016401 A1 | 1/2010 | Aissaoui et al. | |
| 2010/0222328 A1 | 9/2010 | Aissaoui et al. | |
| 2010/0234420 A1 | 9/2010 | Jenck et al. | |
| 2011/0105491 A1 | 5/2011 | Aissaoui et al. | |
| 2011/0212968 A1 | 9/2011 | Aissaoui et al. | |
| 2013/0150424 A1 | 6/2013 | Boss et al. | |
| 2013/0237525 A1 | 9/2013 | Aissaoui et al. | |
| 2013/0324579 A1 | 12/2013 | Bolli et al. | |
| 2015/0166527 A1 | 6/2015 | Boss et al. | |
| 2015/0252032 A1 | 9/2015 | Bolli et al. | |
| 2016/0024064 A1 | 1/2016 | Bolli et al. | |

FOREIGN PATENT DOCUMENTS

| | | |
|---|---|---|
| EP | 2 275 421 | 1/2011 |
| JP | 2001 247569 | 9/2001 |
| WO | WO 2001/096302 | 12/2001 |
| WO | WO 2002/028839 | 4/2002 |
| WO | WO 2002/044172 | 6/2002 |

(Continued)

OTHER PUBLICATIONS

Adam et al., "Stress, Eating and the Reward System", Physiology & Behavior, vol. 91(4), p. 449-458, (2007).

(Continued)

*Primary Examiner* — Barbara P Badio
(74) *Attorney, Agent, or Firm* — Hoxie & Associates LLC

(57) ABSTRACT

The present invention relates to compounds of the formula (I)

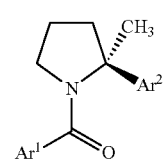

Formula (I)

wherein $Ar^1$ and $Ar^2$ are as described in the description and to their use as pharmaceuticals for the treatment of sundown syndrome. The invention also relates to the preparation of such compounds and of pharmaceutically acceptable salts thereof.

14 Claims, 3 Drawing Sheets

(56) References Cited

FOREIGN PATENT DOCUMENTS

| | | |
|---|---|---|
| WO | WO 2002/089800 | 11/2002 |
| WO | WO 2002/090355 | 11/2002 |
| WO | WO 2003/002559 | 1/2003 |
| WO | WO 2003/002561 | 1/2003 |
| WO | WO 2003/032991 | 4/2003 |
| WO | WO 2003/041711 | 5/2003 |
| WO | WO 2003/051368 | 6/2003 |
| WO | WO 2003/051873 | 6/2003 |
| WO | WO 2004/024725 | 3/2004 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2005/044797 | 5/2005 |
| WO | WO 2005/113522 | 12/2005 |
| WO | WO 2005/118548 | 12/2005 |
| WO | WO 2005/121131 | 12/2005 |
| WO | WO 2006/123249 | 11/2006 |
| WO | WO 2007/039781 | 4/2007 |
| WO | WO 2007/105177 | 9/2007 |
| WO | WO 2008/008517 | 1/2008 |
| WO | WO 2008/020405 | 2/2008 |
| WO | WO 2008/038251 | 4/2008 |
| WO | WO 2008/069997 | 6/2008 |
| WO | WO 2008/081399 | 7/2008 |
| WO | WO 2008/087611 | 7/2008 |
| WO | WO 2008/117241 | 10/2008 |
| WO | WO 2008/139416 | 11/2008 |
| WO | WO 2008/144380 | 11/2008 |
| WO | WO 2008/150364 | 12/2008 |
| WO | WO 2009/003993 | 1/2009 |
| WO | WO 2009/003997 | 1/2009 |
| WO | WO 2009/004584 | 1/2009 |
| WO | WO 2009/016560 | 2/2009 |
| WO | WO 2009/016564 | 2/2009 |
| WO | WO 2009/040730 | 4/2009 |
| WO | WO 2009/047723 | 4/2009 |
| WO | WO 2009/077990 | 6/2009 |
| WO | WO 2009/104155 | 8/2009 |
| WO | WO 2009/124956 | 10/2009 |
| WO | WO 2010/004507 | 1/2010 |
| WO | WO 2010/038200 | 4/2010 |
| WO | WO 2010/048012 | 4/2010 |
| WO | WO 2010/060470 | 6/2010 |
| WO | WO 2010/060471 | 6/2010 |
| WO | WO 2010/060472 | 6/2010 |
| WO | WO 2010/063662 | 6/2010 |
| WO | WO 2010/063663 | 6/2010 |
| WO | WO 2010/072722 | 7/2010 |
| WO | WO 2010/114978 | 10/2010 |
| WO | WO 2010/122151 | 10/2010 |
| WO | WO 2010/143116 | 12/2010 |
| WO | WO 2011/050198 | 4/2011 |
| WO | WO 2011/050200 | 4/2011 |
| WO | WO 2011/050202 | 4/2011 |
| WO | WO 2011/090911 | 7/2011 |
| WO | WO 2012/025877 | 3/2012 |
| WO | WO 2012/039717 | 3/2012 |
| WO | WO 2012/063207 | 5/2012 |
| WO | WO 2012/110986 | 8/2012 |
| WO | WO 2013/068935 | 5/2013 |
| WO | WO 2013/182972 | 12/2013 |
| WO | WO 2014/057435 | 4/2014 |
| WO | WO 2014/141065 | 9/2014 |
| WO | WO 2015/083070 | 6/2015 |
| WO | WO 2015/083071 | 6/2015 |
| WO | WO 2015/083094 | 6/2015 |

OTHER PUBLICATIONS

Aston-Jones et al., "Lateral hypothalamic orexin/hypocretin neurons: A role in 3 reward-seeking and addiction", Brain Research, vol. 1314, p. 1-18, (2009).

Bachman et al., "Sundowning and Other Temporally Associated Agitation States in Dementia Patients", Annual Review of Medicine, vol. 57, p. 499-511, (2006).

Ballard et al., "Management of agitation and aggression associated with Alzheimer disease", Nature Reviews Neurology, vol. 5(5), p. 245-255, (2009).

Berridge et al., "Hypocretin/orexin in arousal and stress", Brain Research, vol. 1314, p. 1-41, (2009).

Borgland et al., "Orexin A in the VTA is Critical for the Induction of Synaptic Plasticity and Behavioral Sensitization to Cocaine", Neuron, vol. 49(4), p. 589-601, (2006).

Boutrel et al., "Role for hypocretin in mediating stress-induced reinstatement of cocaine-seeking behavior", Proceedings of the National Academy of Sciences, vol. 102(52), p. 19168-19173, (2005).

Boss et al., "Biomedical Application of Orexin/Hypocretin Receptor Ligands in Neuroscience", Journal of Medicinal Chemistry, vol. 52(4), p. 891-903, (2009).

Brisbare et al., "Promotion of sleep by targeting the orexin system in rats, dogs and humans", Nature Medicine, 13, p. 150-155, (2007).

Brusco et al., "Melatonin treatment stabilizes chronobiologic and cognitive symptoms in Alzheimer's disease", Neuroendocrinology Letters, vol. 21, p. 39-42, (2000).

Carter et al., "The brain hypocretins and their receptors: mediators of allostatic Arousal", Current Opinion in Pharmacology, vol. 9, p. 1-7, (2009).

Chemelli et al., "Narcolepsy in orexin Knockout Mice: Molecular Genetics of Sleep Regulation", Cell Press, vol. 98, p. 437-451, (1999).

Chemical Abstracts Registry No. 950165-87-4, indexed in the Registry file on STN CAS Online Oct. 11, 2007.

Chrousos et al., "The Concepts of Stress and Stress System Disorders", JAMA, vol. 267(9), p. 1244-1252, (1992).

Cohen-Mansfield et al., "Melatonin for treatment of sundowning in elderly persons with dementia—a preliminary study", Archives of Gerontology and Geriatrics, vol. 31, p. 65-76, (2000).

De Lucca et al., "Nonsymmetric P2/P2' Cyclic Urea HIV Protease Inhibitors. Structure-Activity Relationship, Bioavailability, and Resistance Profile of Monoindazole-Substituted P2 Analogues", Journal of Medicinal Chemistry, vol. 41, p. 2411-2423, (1998).

Dietrich et al., "Intact learning and memory in rats following treatment with the dual orexin receptor antagonist almorexant", Psychopharmacology, vol. 212, p. 145-154, (2010).

Falsetti et al., "Risperidone for control of agitation in dementia patients", Am J Health-Syst. Pharm., vol. 57, p. 862-870, (2000).

Fendt et al., "The neuroanatomical and neurochemical basis of conditioned fear", Neuroscience Biobehavioral Reviews, vol. 23, 743-760, (1999).

Feng et al., "Changes in brain orexin levels in a rat model of depression induced by neonatal administration of clomipramine", J Psychopharmacol, vol. 22(7), p. 1-8, (2008).

Furlong et al., "Hypocretin/orexin contributes to the expression of some but not all forms of stress and arousal", European Journal of Neuroscience, vol. 30(8), p. 1-12, (2009).

Gould et al., "Salt Selection for basic drugs", International Journal of Pharmaceutics, vol. 33, p. 201-217, (1986).

Gozzi, A. et al., "Functional Magnetic Resonance Imaging Reveals Different Neural Substrates for the Effects of Orexin-1 and Orexin-2 Receptor Antagonists", PLoS One (2011), vol. 6, Issue 1, e 16406.

Greene et al., "Protective Groups in Organic Synthesis", Wiley-Interscience, (1999), TOC,ABBR,Index.

Hamamoto et al., "Chemoenzymatic synthesis of the C-13 side chain of paclitaxel (Taxol) and docetaxel (Taxotere)", Tetrahedron: Asymmetry, vol. 11, p. 4485-4497, (2000).

Hollander et al., "Insular hypocretin transmission regulates nicotine reward", Proceedings of the National Academy of Sciences, vol. 105(49), p. 19479-19484, (2008).

Hutcheson et al., "Orexin-1 receptor antagonist SB-334867 reduces the acquisition and expression of cocaine-conditioned reinforcement and the expression of amphetamine-conditioned reward", Behavioural Pharmacology, vol. 22(2), p. 1-9, (2011).

International Search Report of International Application No. PCT/IB2013/059233, dated Feb. 27, 2014, 3 pages.

(56) References Cited

OTHER PUBLICATIONS

International Search Report of International Application No. PCT/IB2014/066548, dated Feb. 27, 2015, 4 pages.
International Search Report of International Application No. PCT/IB2014/059628, dated Aug. 25, 2014, 4 pages.
International Search Report of International Application No. PCT/IB2013/054567, dated Sep. 26, 2013, 3 pages.
Jenck et al., "Promotion of sleep by targeting the orexin system in rats, dogs and humans", Nature Medicine, vol. 13, p. 150-155, (2007).
Jonghe et al., "Effectiveness of melatonin treatment on circadian rhythm disturbances in dementia. Are there implications for delirium? A systematic review", International Journal of Geriatric Psychiatry, vol. 25(12), p. 1201-8, (2010).
Kang et al., "Amyloid-B Dynamics Are Regulated by Orexin and the Sleep-Wake Cycle", Science Express, vol. 326(5955), p. 1-8, (2009).
Kayaba et al., "Attenuated defense response and low basal blood pressure in orexin knockout mice", American Journal of Physiology Regulatory Integrative Comparative Physiology, vol. 285, R581-593, (2003).
Koob et al., "Neurobiological mechanisms of addiction: Focus on corticotropin-releasing factor", Current Opinion Investigational Drugs, vol. 11(1), p. 63-71, (2010).
Lamb et al., "Discovery of molecular switches within the ADX-47273 mGlu5 PAM scaffold that modulate modes of pharmacology to afford potent mGlu5 NAMs, PAMs and partial antagonists", Bioorganic &Medicinal Chemistry Letters, 2010, vol. 21, p. 2711-2714.
Langmead, C.I., et al., "Characterisation of the Binding of [$^3$H]-SB-674042, a Novel Nonpeptide Antagonist, to the Human Orexin-1 Receptor", Brit. I. Pharmacol., vol. 141, p. 340-346, (2004).
Lawrence et al., "The orexin system regulates alcohol-seeking in rats", British Journal of Pharmacology, vol. 148(6), p. 752-759, (2006).
Lesage et al., "Nicotine self-administration in the rat: effects of hypocretin antagonists and changes in hypocretin Mrna", Psychopharmacology, vol. 209(2), p. 203-212, (2010).
Liu et al., "Insomnia and Hypersomnia Associated with Depressive Phenomenology and Comorbidity in Childhood Depression", Sleep and Childhood Depression, vol. 30(1), p. 83-90, (2007).
Mathes et al., "The biology of binge eating", Appetite, vol. 52, p. 545-553, (2009).
Majzoub, I.A. et al., "Corticotropin-Releasing Hormone Physiology", European Journal ofEndocrinology, vol. 155, S71-S76, (2006).
Moorthy et al., "Photoinduced C—Br Homolysis of 2-Bromobenzophenones and Pschorr Ring Closure of 2-Aroylaryl Radicals to Fluorenones", Journal of Organic Chemistry, p. 9786-9, (2007).
National Center for Biotechnology Information. PubChem Compound Database; CID=16672186, https://pubchem.ncbi.nlm.nih.gov I compound/16672186 (accessed Mar. 1, 2016), 11 pages.
Nollet et al., "Activation of orexin neurons in dorsomedial/perifornical hypothalamus and antidepressant reversal in a rodent model of depression", NeuroPharmacology, vol. 61(1-2), p. 1-11, (2011).
Packiarajan et al., "Azetidinyl oxadiazoles as potent mGluR5 positive allosteric modulators", Bioorganic & Medicinal Chemistry Letters, vol. 22, p. 6469-6474, (2012).
Panetta et al., "Disulfide-Functionalized 3-, 4-, 5-, and 6-Substituted 2,2'-Bipyridines and their Ruthenium Complexes", Journal of Organic Chemistry, vol. 64(3), p. 1015-1021, (1999).
Powers et al., "Synthesis of methyl-, fluoro-, and chloro-substituted 6- hydroxyisoindolin-l-ones", Tetrahedron Letters, p. 1267-1269, (2009).
Prud'homme et al., Nutritional Status Modulates Behavioural and Olfactory Bulb Fos Response to Isoamyl Acetate or Food Odour in Rats: Roles of Orexins and Leptin, Neuroscience, vol. 162(4), p. 1287-1298, (2009).
Remington, The Science and Practice of Pharmacy, 21st Edition (2005), Part 5, Pharmaceutical Manufacturing, (book cover and table of contents).
Salomon, R.M. et al.,"Diurnal Variation of Cerebospinal Fluid Hypocretin-1 (Orexin A) Levels in Control and Depressed Subjects", Biol. Psychiatry, vol. 54, p. 96-104, (2003).
Sakurai, T. et al., Orexins and Orexin Receptors: A Family of Hypothalamic Neuropeptides and G Protein-Coupled Receptors that Regulate Feeding Behavior, Cell, vol. 92, p. 573-585, (1998).
Saper et al., "Hypothalamic regulation of sleep and circadian rhythms", Nature, vol. 437, p. 1257-1263, (2005).
Stahl, P.H., et al. Handbook of Pharmaceutical Salts. Properties, Selection and Use., (title page, appendix, and pp. 330-350, (2008), ISBN-I 0 3-906390-58-6, ISBN-13 978-3-906390-58-1, Verlag Helvetica Chimica Acta, Zurich, Switzerland.
Tsujino et al., "Orexin/Hypocretin: A Neuropeptide at the Interface of Sleep, Energy Homeostasis, and Reward System", Pharmacological Review, vol. 61(2), p. 162-176, (2009).
Quarta et al., "The orexin-1 receptor antagonist SB-334867 reduces amphetamine-evoked dopamine outflow in the shell of the nucleus accumbens and decreases the expression of amphetamine sensitization", Neurochemistry International, vol. 56(1), p. 11-15, (2009).
Sharf et al., "Role of orexin/hypocretin in dependence and addiction", Brain Research, vol. 1314, p. 130-138, (2010).
Shippenberg et al., "Recent Advances in Animal Models of Drug Addiction", Neuropsychopharmacalogy, Chp. 97, p. 1381-1397, (2002).
Smith et al., "Orexin / hypocretin signaling at the OX1 receptor regulates cue-elicited cocaine-seeking", Eur Journal Neuroscience, vol. 30(3), p. 493-503, (2009).
Smith et al., "Orexin/hypocretin is necessary for context-driven cocaine-seeking", Neuropharmacology, vol. 58(1), p. 1-6, (2010).
Spealman et al, "Pharmacological and Environmental Determinants of Relapse to Cocaine-Seeking Behavior", Pharmacology Biochemistry and Behavior, vol. 64(2), p. 327-336, (1999).
Stasi et al., "Discovery, synthesis, selectivity modulation and DMPK characterization of 5 -azaspiro[2.4]heptanes as potent orexin receptor Antagonists", Bioorganic & Medicinal Chemistry Letters, vol. 23(9), p. 2653-2656, (2013).
Stickgold et al., "Sleep-dependent memory consolidation", Nature, vol. 437, p. 1272-1278, (2005).
Stopa et al., "Pathologic evaluation of the human suprachiasmatic nucleus in severe dementia", J Neuropathol Exp Neurol., vol. 58(1), p. 29-39, (1999).
Sutcliffe et al., "The Hypocretins: Setting the arousal threshold", Nature Reviews Neuroscience, vol. 3, p. 339-349, (2002).
Swaab et al., "The Suprachiasmatic Nucleus of the Human Brain in Relation to Sex, Age, and Senile Dementia", Brain Research, vol. 342, p. 37-44, (1985).
Swaab et al., "τ and ubiquitin in the human hypothalamus in aging and Alzheimer's disease", Brain Research, p. 239-249, (1992).
Vanderschuren et al., "Sensitization Processes in Drug Addiction", Current Topics in Behavioral Neurosciences, vol. 3, p. 179-195, (2009).
Vinkers et al., "Translational aspects of pharmacological research into anxiety disorders: The stress-induced hyperthermia (SIH) paradigm", European Journal of Pharmacology, vol. 585, p. 407-425, (2008).
Winrow et al., "Orexin receptor antagonism prevents transcriptional and behavioral plasticity resulting from stimulant exposure", Neuropharmacology, vol. 58(1), p. 1-10, (2009).
Wouters et al.,"Pharmaceutical Salts and Co-crystals", RCS Drug Discovery, No. 16, p. vii-xiv, (2012).
Zhang et al., "Multiple components of the defense response depend on orexin: Evidence from orexin knockout mice and orexin neuron-ablated mice", Autonomic Neuroscience, vol. 126-127, p. 139-145, (2006).

(56) References Cited

OTHER PUBLICATIONS

Zhou et al., "VIP neurons in the human SCN in relation to sex, age, and Alzheimer's disease", Neurobiol. Aging, vol. 16(4), p. 571-576, (1995).
U.S. Appl. No. 15/644,547, filed Jul. 7, 2017, Boss et al.

USE OF BENZIMIDAZOLE-PROLINE DERIVATIVES

CROSS REFERENCE TO RELATED APPLICATIONS

This application is a United States Application under 35 U.S.C. 371 claiming benefit of PCT Application No. PCT/IB2014/066548, filed on Dec. 3, 2014, which claims the benefit of PCT Application No. PCT/IB2013/060630, filed on Dec. 4, 2013, the contents of each of which are incorporated herein by reference.

The present invention relates to novel benzimidazole-proline derivatives of formula (I) and their use as pharmaceuticals for the treatment of sundown syndrome. The invention also concerns related aspects including processes for the preparation of the compounds and pharmaceutical compositions containing one or more compounds of formula (I).

Sundown syndrome is a late-day circadian syndrome of increased confusion and restlessness, generally in a patient with some form of dementia. Cardinal clinical signs include increased agitation, general confusion and mood swings that typically develop as natural light begins to fade. This disruptive behavior worsening in the late afternoon or early evening among dementia patients or elderly institutionalized patients has been reported in the medical literature for more than 60 years (Bachman & Rabins, Annu. Rev. Med. 2006. 57:499-511). Terms used to describe this phenomenon include sundowning, afternoon sundowning, sundowner syndrome, or sundowning syndrome.

In contrast to delirium which is generally acute in onset and fluctuating in the course of the day, sundown syndrome is defined by its temporal pattern (late-day onset and termination).

Sundown syndrome seems to occur more frequently during the middle stages of Alzheimer dementia. Patients are generally able to understand that this behavioral pattern is abnormal. Sundown syndrome seems to subside with the progression of a patient's dementia.

About half of dementias (44%) are of Alzheimer's type including Alzheimer dementia (presenile dementia or senile dementia), subcortical dementia, diffuse Lewy body dementia, and frontotemporal dementia. About 20-45% of Alzheimer type patients will experience some sort of sundowning confusion. Further 47% of dementias are of vascular type including vascular dementia, multi-infarct dementia, Binswanger's dementia, boxer's dementia, and arteriosclerotic dementia. Remaining types of dementia (9%) are of other etiologies such as paralytic dementia, substance-induced persisting dementia, dialysis dementia, hydrocephalic dementia, tumors, subdural hematoma, normal pressure hydrocephalus, vasculitis, Vitamin deficiency, or endocrine and metabolic disease.

Possible etiology of sundown syndrome includes the particular histopathological signs of degeneration that are reported into Ventro Lateral Pre-Optic area (VLPO) and Supra-Chiasmatic Nucleus (SCN) in dementias. The SCN pacemaker is severely affected in Alzheimer disease, whereas pineal is essentially unaffected (Swaab D F, Fliers E, Partiman T S. "The suprachiasmatic nucleus of the human brain in relation to sex, age and senile dementia". Brain Res 1985; 342: 37-44; Zhou J N, Hofman M A, Swaab D F. "VIP neurons in the human SCN in relation to sex, age, and Alzheimer's disease". Neurobiol Aging 1995; 16: 571-576; Swaab D F, Grundke-lqbal I, Iqbal K et al. "Tau and ubiquitin in the human hypothalamus in aging and Alzheimer's disease". Brain Res 1992; 590: 239-249; Stopa E G, Volicer L, Kuo-Leblanc V et al. "Pathologic evaluation of the human suprachiasmatic nucleus in severe dementia". J Neuropathol Exp Neurol 1999; 58: 29-39). SCN is associated with regulating wakefulness and sleep patterns by maintaining circadian rhythms. These rhythms are synchronized with external light-dark cues and involve complex neurobiological regulation within the brain. Histopathological signs of geriatric disturbance in brain circadian oscillators such as SCN have been observed across several mammalian species.

The most widely prescribed pharmacological treatments for sundown syndrome—atypical antipsychotics—have a modest but significant beneficial effect in the short-term treatment (over 6-12 weeks) of aggression, less so on symptoms of agitation, and have limited benefits in longer term therapy. Concerns are growing over the potential for serious adverse outcomes with these treatments, including stroke and death (Ballard et al., Nat. Rev. Neurol. 5, 245-255, 2009).

Previous clinical work has been published and describes medical technology with protocols for evaluating drug effects in sundown syndrome patients; a review on trials and methodology in agitation and aggression in dementia can be found in Ballard et al., Nat. Rev. Neurol. 5, 245-255, 2009 (see especially table 1). Published studies are for example:
a) Cohen-Mansfield J, Garfinkel D, Lipson S. Melatonin for treatment of sundowning in elderly persons with dementia—a preliminary study. Arch Gerontol Geriatr 2000; 31: 65-76.
b) Brusco L I, Marquez M, Cardinali D P. Melatonin treatment stabilizes chronobiologic and cognitive symptoms in Alzheimer's disease. Neuroendocrinol Lett 2000; 21: 39-42.
c) de Jonghe A, Korevaar J C, van Munster B C, de Rooij S E. Effectiveness of melatonin treatment on circadian rhythm disturbances in dementia. Are there implications for delirium? A systematic review. Int J Geriatr Psychiatry. 2010 December; 25(12):1201-8.
d) Falsetti A E. Risperidone for control of agitation in dementia patients. Am J Health Syst Pharm. 2000 May 1; 57(9):862-70.

Partial effectiveness of melatonin or bright light exposure has been reported to decrease behavioral symptoms in sundown syndrome. Consistent sleeping schedule and daily routine can also reduce confusion and agitation. Reduction of daytime napping is recommended as unintentionally getting too much sleep will affect nighttime sleep. Reduction of caffeine intake is recommended to sundown syndrome patients.

Neuronal afferences and efferences connect hypothalamic orexin neurons to brain areas involved in circadian rhythm regulation (receiving day-night signals) and in cortical activation (inducing and maintaining alertness); orexin neurons also receive afferent physiological and emotional inputs of limbic and metabolic origin. Activated orexin neurons thus regulate alertness for adapting the organism to environmental and circadian requirements and for accurate maintenance of homeostatic balance (Saper et al., Nature 437: 1257, 2005). The Ventro Lateral Pre-Optic area (VLPO) and the Supra-Chiasmatic Nucleus (SCN) are important brain clock regions that exert major inhibition on activity of orexin neurons during the nocturnal phase. It is hypothesized that abnormally hyperactive orexin neurons significantly contribute to cortical overdrive mediating hyperalertness at a given time point in the circadian cycle. Pathological orexin hyperactivity may result from deficient inhibitory input from VLPO and SCN that should start to gradually establish in late afternoon.

Caffeine administration increases orexin levels in rat brain. Caffeine may be used as a tool to experimentally simulate deficient inhibitory VLPO-SCN input to hypothalamic orexin neurons. The pharmacological action of caffeine, an adenosine A1 and A2A receptor antagonist, is to block adenosinergic inhibition exerted by adenosinergic neurons upon orexin neurons.

The orexin receptor antagonists of the present invention may reverse late-day agitation simulated in animals by afternoon caffeine administration. Electroencephalographic recordings confirm the behavioral symptoms of agitation which were reduced by two of the exemplified compounds when administered orally to rats and/or dogs.

SHORT DESCRIPTION OF THE FIGURES

Figure 1:
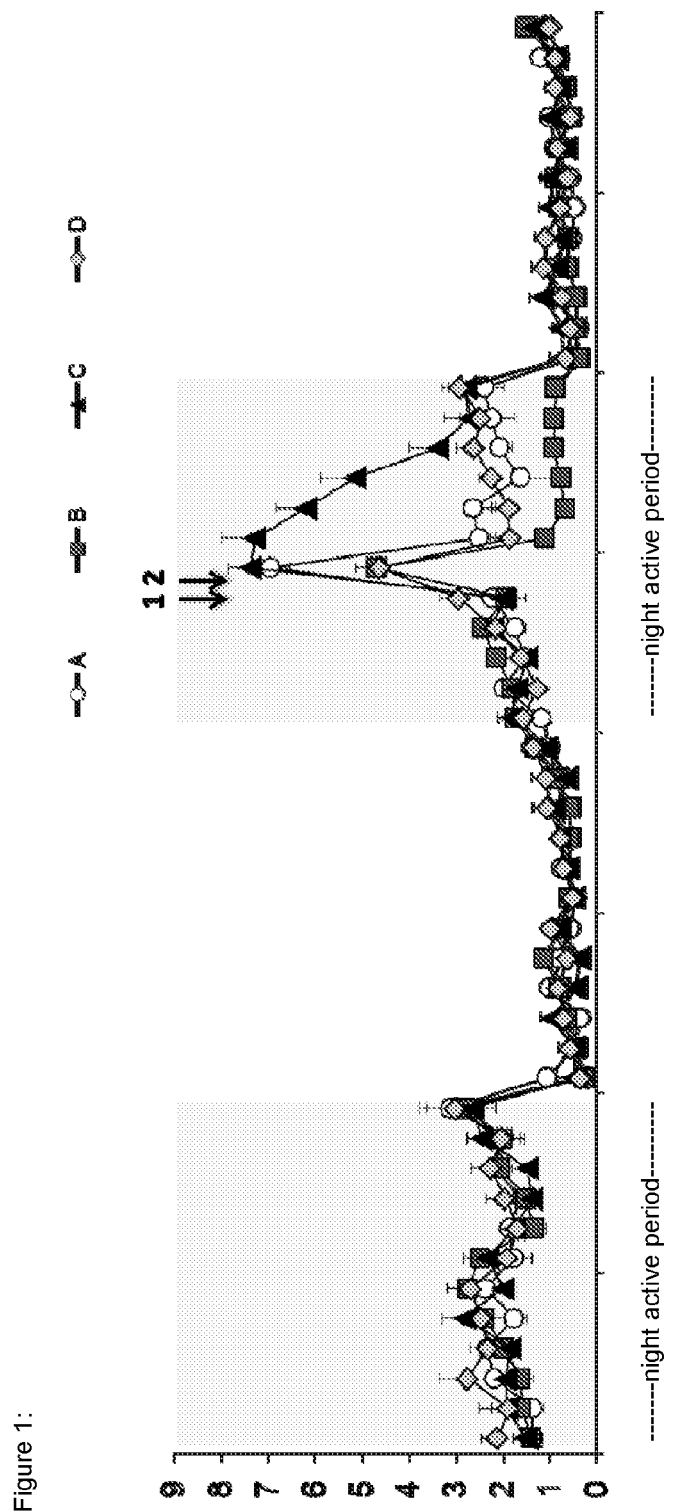
FIG. 1 shows the effect of the compound of example 7 in a coffein-induced agitation model in the rat.

Orexin receptor antagonists comprising a 2-substituted saturated cyclic amide derivatives (such as 2-substituted pyrrolidine-1-carboxamides) are known for example from WO2008/020405, WO2008/038251, WO2008/081399, WO2008/087611, WO2008/117241, WO2008/139416, WO2009/004584, WO2009/016560, WO2009/016564, WO2009/040730, WO2009/104155, WO2010/004507, WO2010/038200, WO2001/096302, WO2002/044172, WO2002/089800, WO2002/090355, WO2003/002559, WO2003/032991, WO2003/041711, WO2003/051368, WO2003/051873, WO2004/026866, WO2004/041791, WO2004/041807, WO2004/041816, WO2009/003993, WO2009/003997, WO2009/124956, WO2010/060470, WO2010/060471, WO2010/060472, WO2010/063662, WO2010/063663, WO2010/072722, WO2010/122151, and WO2008/150364. A particular pyrrolidine derived compound is disclosed in Langmead et. al, Brit. J. Pharmacol. 2004, 141, 340-346 as being highly orexin-1 selective. WO2003/002561 discloses certain N-aroyl cyclic amine derivatives, encompassing benzimidazol-2-yl-methyl substituted pyrrolidine derivatives, as orexin receptor antagonists. There is no mention of sundown syndrome in WO2003/002561. Despite the great number of prior art orexin receptor antagonist compounds and their high structural variability, all compounds share a common structural feature, i.e. in position 2 of the saturated cyclic amide a linker group such as at least a methylene group (or longer groups such as —$CH_2$—NH—CO—, —$CH_2$—NH—, —$CH_2$—O—, —$CH_2$—S—, etc.) link the cyclic amide to the respective aromatic ring system substituent. It has now surprisingly been found that, despite the substantial conformational changes that may be expected from the removal of a linker between two rigid structural elements, the present compounds, that have a benzimidazole ring directly attached to a pyrrolidine amide in position 2, are potent orexin receptor antagonists.

The present invention now provides certain benzimidazole-proline derivatives, which are potent non-peptide antagonists of human orexin receptors for use in the prevention or treatment of sundown syndrome.

1) A first aspect of the invention relates to compounds of the formula (I):

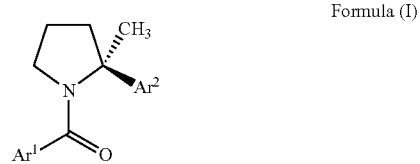

Formula (I)

for use in the prevention or treatment of sundown syndrome; wherein the compounds of formula (I) are in absolute configuration (S);
$Ar^1$ represents

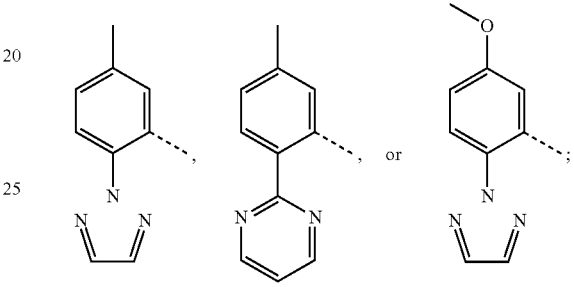

and $Ar^2$ represents

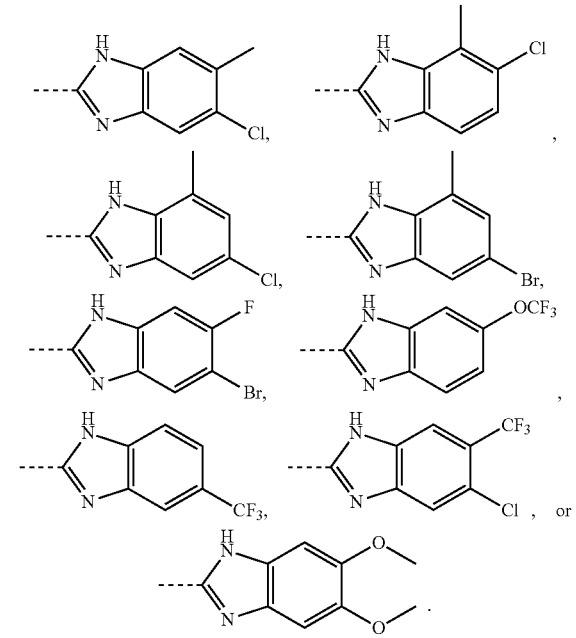

2) A second embodiment relates to compounds of formula (I) according to embodiment 1) for use according to embodiment 1), wherein the compound is:

[(S)-2-(5-Chloro-4-methyl-1H-benzoimidazol-2-yl)-2-methyl-pyrrolidin-1-yl]-(5-methyl-2-pyrimidin-2-yl-phenyl)-methanone;

[(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone;

[(S)-2-(5-Bromo-7-methyl-1H-benzoimidazol-2-yl)-2-methyl-pyrrolidin-1-yl]-(5-methyl-2-pyrimidin-2-yl-phenyl)-methanone;
[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone;
[(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone;
[(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone;
[(S)-2-(5,6-Dimethoxy-1H-benzoimidazol-2-yl)-2-methyl-pyrrolidin-1-yl]-(5-methyl-2-pyrazol-1-yl-phenyl)-methanone;
[(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone;
[(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone;
(5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone; or
(5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone.

3) A third embodiment relates to compounds according to embodiment 1) for use according to embodiment 1), wherein the compound is:
[(S)-2-(5-Bromo-7-methyl-1H-benzoimidazol-2-yl)-2-methyl-pyrrolidin-1-yl]-(5-methyl-2-pyrimidin-2-yl-phenyl)-methanone.

4) A fourth embodiment relates to compounds according to embodiment 1) for use according to embodiment 1), wherein the compound is:
[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone.

The compounds of formula (I) contain at least one stereogenic center which is situated in position 2 of the pyrrolidine moiety. The absolute configuration of the pyrrolidine moiety of the present compounds is as depicted in formula (I); i.e. said chiral center is in absolute (S) configuration.

In addition, it is well understood that the benzimidazole moiety $Ar^2$ of the present compounds represents tautomeric forms. Thus, substituents of the benzimidazole moiety may be attached in the position(s) ortho to the bridgehead atoms (i.e. attached in position(s) 4 and/or 7), and/or in the position(s) meta to the bridgehead atoms, (i.e. attached in position(s) 5 and/or 6). It is understood that the two ortho, and, respectively, the two meta positions are considered equivalent. For example, the group 5-chloro-4-methyl-1H-benzoimidazol-2-yl is understood to signify the same group as 6-chloro-7-methyl-1H-benzoimidazol-2-yl, 5-chloro-4-methyl-3H-benzoimidazol-2-yl and 6-chloro-7-methyl-3H-benzoimidazol-2-yl.

In this patent application, a dotted line shows the point of attachment of the radical drawn. For example, the radical drawn below

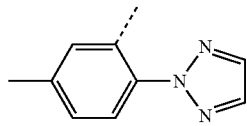

represents a 5-methyl-2-(2-triazolyl)-phenyl group.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012. A preferred pharmaceutically acceptable salt is the hydrochloric acid salt.

Sundown syndrome is defined as a late-day (i.e. afternoon and/or evening hours, especially afternoon hours) circadian syndrome of increased confusion and restlessness in a patient, wherein in general said patient has some form of dementia. Cardinal clinical signs include increased agitation, general confusion and mood swings that typically develop as natural light begins to fade. The term "late day" referred to herein relates to the afternoon and evening, notably the time about sunset and later (but not including the night/the sleep time); for example the time from about 4 pm to about 10 pm, especially from about 4 pm to about 9 pm. In one sub-embodiment, the term relates to the afternoon, especially from about 4 pm to about 7 pm; in another sub-embodiment the term relates to the evening, especially from about 7 pm to about 10 pm.

Dementias include notably dementias of Alzheimer's type including: Alzheimer dementia (presenile dementia or senile dementia), subcortical dementia, diffuse Lewy body dementia, and frontotemporal dementia. Dementias further include dementias of vascular type such as: vascular dementia, multi-infarct dementia, Binswanger's dementia, boxer's dementia, arteriosclerotic dementia. Remaining types of dementia (9%) are of other etiologies such as paralytic dementia, substance-induced persisting dementia, dialysis dementia, hydrocephalic dementia, and dementias due to tumors, subdural hematoma, normal pressure hydrocephalus, vasculitis, Vitamin deficiency, or endocrine or metabolic disease. In the context of the present invention, the term preferably refers to dementias of Alzheimer's type, especially Alzheimer dementia. It is understood that the term dementia also includes any combination of the above listed types of dementias.

In a sub-embodiment, dementia especially refers to middle stages of dementias of Alzheimer's type (especially to middle stages of Alzheimer dementia) in which stages sundown syndrome appears to occur more frequently and/or of mixed dementia [a form of dementia combining neuropathological protein deposits (associated with Alzheimer dementia) with a dementia of vascular type]. In a preferred sub-embodiment, dementia refers to middle stages of dementias of Alzheimer's type (especially to middle stages of Alzheimer dementia).

Stages of dementias of Alzheimer's type may be defined as follows (wherein the above-mentioned middle stages of dementias of Alzheimer's type (especially middle stages of Alzheimer dementia) refer to stages 3 to 6, preferably stages 3 to 5, in particular to stages 3 and 4 as defined below, and wherein pre-senile dementia may be defined as corresponding to stages 1 to 4, in particular to stages 3 and 4, below):

Stage 1: No impairment (normal function); The person does not experience any memory problems. An interview with a medical professional does not show any evidence of symptoms of dementia. Stage 2: Very mild cognitive decline (may be normal age-related changes or earliest signs of a dementia, e.g. of Alzheimer's type): The person may feel as if he or she is having memory lapses (e.g. forgetting familiar words or the location of everyday objects). But at this stage, no symptoms of dementia can be detected during a medical examination or by friends, family or co-workers. Stage 3: Mild cognitive decline (dementia, e.g. of Alzheimer's type can be diagnosed in some, but not all individuals with these symptoms): Friends, family or co-workers begin to notice difficulties. During a detailed medical interview, doctors may be able to detect problems in memory or concentration. Common stage 3 difficulties include: noticeable problems coming up with the right word or name; trouble remembering names when introduced to new people; having noticeably greater difficulty performing tasks in social or work settings; forgetting material that one has just read; losing or misplacing a valuable object; increasing trouble with planning or organizing. Stage 4: Moderate cognitive decline: At this point, a careful medical interview should be able to detect clear-cut symptoms in several areas: forgetfulness of recent events; impaired ability to perform challenging mental arithmetic; greater difficulty performing complex tasks, such as planning dinner for guests, paying bills or managing finances; forgetfulness about one's own personal history; becoming moody or withdrawn, especially in socially or mentally challenging situations. Stage 5: Moderately severe cognitive decline: gaps in memory and thinking are noticeable, and individuals begin to need help with day-to-day activities. At this stage, those with a dementia, e.g. of Alzheimer's type may be unable to recall their own address or telephone number or the high school or college from which they graduated; become confused about where they are or what day it is; have trouble with less challenging mental arithmetic; need help choosing proper clothing for the season or the occasion; still remember significant details about themselves and their family; still require no assistance with eating or using the toilet. Stage 6: Severe cognitive decline: Memory continues to worsen, personality changes may take place and individuals need extensive help with daily activities. At this stage, individuals may lose awareness of recent experiences as well as of their surroundings; remember their own name but have difficulty with their personal history; distinguish familiar and unfamiliar faces but have trouble remembering the name of a spouse or caregiver; need help dressing properly and may, without supervision, make mistakes such as putting pyjamas over daytime clothes or shoes on the wrong feet; experience major changes in sleep patterns (e.g. sleeping during the day and becoming restless at night); need help handling details of toileting; have increasingly frequent trouble controlling their bladder or bowels; experience major personality and behavioral changes, including suspiciousness and delusions (such as believing that their caregiver is an impostor) or compulsive, repetitive behavior like hand-wringing or tissue shredding; tend to wander or become lost. Stage 7: Very severe cognitive decline: In the final stage of e.g. Alzheimer dementia, individuals lose the ability to respond to their environment, to carry on a conversation and, eventually, to control movement. They may still say words or phrases. At this stage, individuals need help with much of their daily personal care, including eating or using the toilet. They may also lose the ability to smile, to sit without support and to hold their heads up. Reflexes become abnormal, muscles grow rigid, swallowing impaired.

5) A fifth embodiment thus relates to compounds according to any one of embodiments 1) to 4) for use according to embodiment 1), wherein the compound is used for the prevention or treatment of sundown syndrome in a patient who has some form of dementia.

Medical factors which may contribute to the development of sundown syndrome said patients expressing some form of dementia may be chronic pain (e.g. due to arthritis or malignancy) organ systemic disorders (e.g. congestive heart failure, ischemic heart diesease, asthma, chronic obstructive pulmonary disease, gastroesophageal reflux, incontinence, benign prostatic hypertrophy), psychiatric conditions (e.g. depression, anxiety, psychosis), and effects of medication.

6) A further embodiment relates to compounds according to any one of embodiments 1) to 4) for use according to embodiment 5), wherein said patient has a dementia of Alzheimer's type.

7) A further embodiment relates to compounds according to any one of embodiments 1) to 4) for use according to embodiment 5), wherein said patient has Alzheimer dementia.

8) A further embodiment relates to compounds according to any one of embodiments 1) to 4) for use according to embodiment 5), wherein said patient has middle stage dementia of Alzheimer's type (especially middle stage Alzheimer dementia).

9) A further embodiment relates to compounds according to any one of embodiments 1) to 4) for use according to any one of embodiments 1) to 8), wherein said sundown syndrome is afternoon sundown syndrome (wherein afternoon is especially defined as the interval) from about 4 pm to about 7 pm).

10) A further embodiment relates to compounds according to any one of embodiments 1) to 4) for use according to any one of embodiments 1) to 8), wherein said sundown syndrome is evening sundown syndrome (wherein afternoon is especially defined as the interval) from about 7 pm to about 10 pm).

The invention, thus, relates to compounds of the formula (I) as defined in embodiment 1), or to such compounds further limited by the characteristics of any one of embodiments 2) to 4), under consideration of their respective dependencies; to pharmaceutically acceptable salts thereof; and to the use of such compounds as medicaments in the treatment of sundown syndrome according to any one of embodiments 1) to 10). For avoidance of any doubt, the following embodiments are thus possible and intended and herewith specifically disclosed in individualized form:
1, 2+1, 3+1, 4+1, 5+1, 5+2+1, 5+3+1, 5+4+1, 6+5+1, 6+5+2+1, 6+5+3+1, 6+5+4+1, 7+5+1, 7+5+2+1, 7+5+3+1, 7+5+4+1, 8+5+1, 8+5+2+1, 8+5+3+1, 8+5+4+1, 9+1, 9+2+1, 9+3+1, 9+4+1, 9+5+1, 9+5+2+1, 9+5+3+1, 9+5+4+1, 9+6+5+1, 9+6+5+2+1, 9+6+5+3+1, 9+6+5+4+1, 9+7+5+1, 9+7+5+2+1, 9+7+5+3+1, 9+7+5+4+1, 9+8+5+1, 9+8+5+2+1, 9+8+5+3+1, 9+8+5+4+1, 10+1, 10+2+1, 10+3+1, 10+4+1, 10+5+1, 10+5+2+1, 10+5+3+1, 10+5+4+1, 10+6+5+1, 10+6+5+2+1, 10+6+5+3+1, 10+6+5+4+1, 10+7+5+1, 10+7+5+2+1, 10+7+5+3+1, 10+7+5+4+1, 10+8+5+1, 10+8+5+2+1, 10+8+5+3+1, 10+8+5+4+1.

In the list above the numbers refer to the embodiments according to their numbering provided hereinabove whereas "+" indicates the dependency from another embodiment. The different individualized embodiments are separated by commas. In other words, "10+7+5+1" for example refers to embodiment 10) depending on embodiment 7), depending on embodiment 5), depending on embodiment 1), i.e. embodiment "10+7+5+1" corresponds to the compounds of formula (I) according to embodiment 1) further limited by all the features of the embodiments 5), 7), and 10).

The compounds of formula (I) according to any one of embodiments 1) to 4) and their pharmaceutically acceptable salts can be used as medicaments for the prevention or treatment of sundown syndrome, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formulae (I), (II) and (III) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the treatment of a disorder mentioned herein comprising administering to a subject a pharmaceutically active amount of a compound of formula (I) as defined in any one of embodiments 1) to 4).

In a preferred embodiment of the invention, the administered amount of such a compound of formula (I) according to any one of embodiments 1) to 4) is comprised between 1 mg and 1000 mg per day, particularly between 5 mg and 400 mg per day, more particularly between 5 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C. In the particular case of time points, the term "about" placed before a certain time point "Y" refers in the current application to an interval extending from the time point Y minus 1 hour to Y plus 1 hour, and preferably to an interval extending from Y minus 30 minutes to Y plus 30 minutes.

For avoidance of any doubt, if compounds are described as useful for the prevention or treatment of certain diseases, such compounds are likewise suitable for use in the preparation of a medicament for the prevention or treatment of said diseases.

Preparation of Compounds of Formula (I):

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products.

Compounds of formula (I) of the present invention can be prepared according to the general sequence of reactions outlined below wherein $Ar^1$ and $Ar^2$ are as defined for formula (I). The generic substituent $(R)_n$ refers to the substituents of the benzimidazole group $Ar^2$ as defined for the compounds of formula (I).

There are two general synthetic approaches towards the compounds of formula (I).

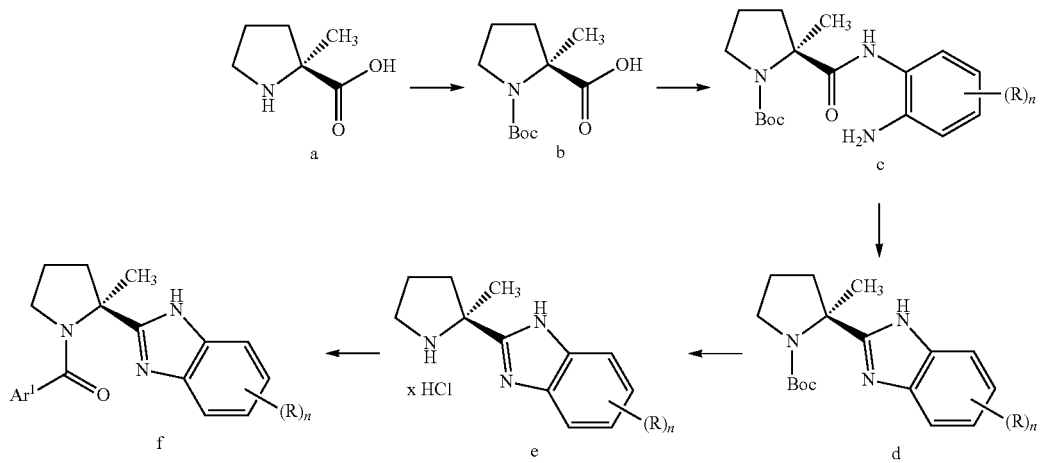

A first synthetic approach 1 may start with a Boc-protection of the respective proline derivative a under standard conditions, e.g. by dissolving the proline a in a solvent such as DCM or THF and adding a base to the solution, for example DIPEA, TEA or aq. Na$_2$CO$_3$ followed by the addition of Boc$_2$O. The reaction is performed at RT and is usually complete within a few hours and results in the Boc-protected proline derivative b. The protected proline derivative b (which is also commercially available) is then coupled under standard amide coupling conditions with the appropriate phenylene-diamine derivative, e.g. in a solvent such as THF, DCM or DMF in the presence of a coupling agent such as HBTU or TBTU or the like and a base, for example DIPEA or TEA to give compound c. Ring closure to obtain the benzimidazole derivative d is achieved for example by dissolving the precursor c in AcOH and heating at 100° C. for 1 h. Compound d is Boc-deprotected under standard acidic conditions such as 4M HCl in dioxane, or TFA in DCM, to give precursor e which is converted into the final compound f by an amide coupling reaction with Ar$^1$—COOH, e.g. in a solvent such as THF, DMF or DCM in the presence of a coupling agent such as TBTU, HBTU, HATU, EDC or the like and a base such as DIPEA, TEA or N-methylmorpholine.

μm) column, a Daicel ChiralPak IB (5 μm) column, a Daicel ChiralPak IC (5 μm) column, or a (R,R)-Whelk-01 (5 μm) column. Typical conditions of chiral HPLC are an isocratic mixture of eluent A (EtOH, in presence or absence of a base like TEA and/or diethylamine or of an acid like TFA) and eluent B (heptane).

The following examples are provided to illustrate the invention. These examples are illustrative only and should not be construed as limiting the invention in any way.

EXPERIMENTAL PART

Abbrevations (as Used Herein and in the Description Above)

Ac Acetyl (such as in OAc=acetate)
AcOH Acetic acid
anh. Anhydrous
aq. aqueous
atm Atmosphere
Boc tert-Butoxycarbonyl
Boc$_2$O di-tert-Butyl dicarbonate

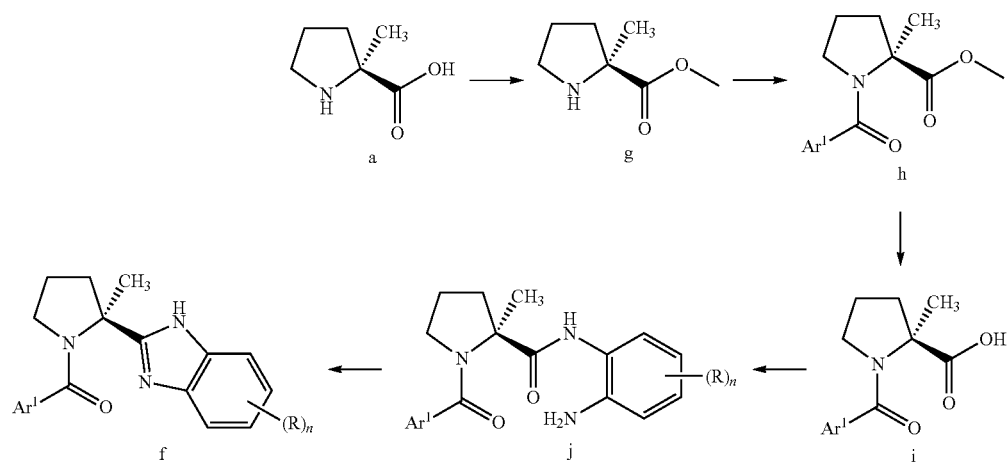

An alternative synthetic approach 2 may start with an esterification (usually methyl ester formation) of the proline derivative a, e.g. by dissolving the starting material in THF and adding 5 equivalents of the respective alcohol (usually MeOH) followed by the addition of EDC and DMAP. The methyl-ester derivative g (which is also commercially available) is then acylated with Ar$^1$—COOH using standard amide coupling conditions such as those described above to result in intermediate h. Ester hydrolysis under standard conditions, e.g. by dissolving the ester derivative h in THF/MeOH=1/1 followed by the addition of 2 eq of aq. 1M NaOH solution results in the carboxylic acid derivative i. The final compounds f are obtained via precursor j by applying the same conditions as described for the amide-coupling and the cyclization in synthetic approach 1.

Whenever compounds of formula (I) are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 μm) column, a Daicel ChiralCel OD-H (5 μm) column, a Daicel ChiralCel OD (10 μm) column, a Daicel ChiralPak IA (5

BSA Bovine serum albumine
Bu Butyl such as in tBu=tert-butyl=tertiary butyl
CC Column Chromatography over silica gel
CHO Chinese Hamster Ovary
conc. Concentrated
DCE 1,2-Dichloroethane
DCM Dichloromethane
DEA Diethylamine
DIPEA Diisopropylethylamine
DMF N,N-Dimethylformamide
DMSO Dimethyl sulfoxide
EDC 3-(Ethyliminomethyleneamino)-N,N-dimethylpropan-1-amine
ELSD Evaporative Light-Scattering Detection
eq Equivalent(s)
ES Electron spray
Et Ethyl
Et$_2$O Diethyl ether
EtOAc Ethyl acetate
EtOH Ethanol
Ex. Example (compound of example)
FC Flash Column Chromatography on silica gel
FCS Foatal calf serum FLIPR Fluorescent imaging plate reader
h Hour(s)
HATU 1-[Bis(dimethylamino)methylene]-1H-1,2,3-triazolo[4,5-b]pyridinium 3-oxid hexafluorophosphate
HBSS Hank's balanced salt solution
HBTU N,N,N',N'-Tetramethyl-O-(1H-benzotriazol-1-yl)uronium hexafluorophosphate
HEPES 4-(2-Hydroxyethyl)-piperazine-1-ethanesulfonic acid
$^1$H-NMR Nuclear magnetic resonance of the proton
HPLC High performance liquid chromatography
LC-MS Liquid chromatography—Mass Spectroscopy
Lit. Literature
M Exact mass (as used for LC-MS)
Me Methyl
MeCN Acetonitrile
MeOH Methanol
MeI Methyl iodide
MHz Megahertz
μl microliter
min Minute(s)
MS Mass spectroscopy
N Normality
Pd(OAc)$_2$ Palladium diacetate
Pd(PPh$_3$)$_4$ Tetrakis(triphenylphosphine)palladium(0)
PL-HCO$_3$ Polymer supported hydrogen carbonate
Ph Phenyl
PPh$_3$ Triphenylphosphine
prep. Preparative
RT Room temperature
sat. Saturated
TBTU O-(Benzotriazol-1-yl)-N,N,N',N'-tetramethyluronium tetrafluoroborate
TEA Triethylamine
TFA trifluoroacetic acid
Tf Trifluoromethansulfonyl
THF Tetrahydrofuran
$t_R$ Retention time
UV Ultra violet
I—Chemistry All temperatures are stated in ° C. The commercially available starting materials were used as received without further purification. Compounds are purified by flash column chromatography over silica gel (FC), column chromatography over silica gel (CC), or by preparative HPLC. Compounds described in the invention are characterized by LC-MS (retention time $t_R$ is given in min.; molecular weight obtained from the mass spectrum is given in g/mol, using the conditions listed below). If the mass is not detectable the compounds are also characterized by $^1$H-NMR (400 MHz: Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz).

Preparative HPLC for Purification of Compounds (Conditions C)

Column: Waters XBridge (10 μm, 75×30 mm). Conditions: MeCN [eluent A]; water+0.5% NH$_4$OH (25% aq.) [eluent B]; Gradient: 90% B→5% B over 6.5 min. (flow: 75 ml/min.). Detection: UV+ELSD.

Preparative HPLC for Purification of Compounds (Conditions D)

Column: Waters Atlantis T3 OBD (10 μm, 75×30 mm). Conditions: MeCN [eluent A]; water+0.5% HCOOH [eluent B]; Gradient: 90% B→5% B over 6.4 min. (flow: 75 ml/min.). Detection: UV+ELSD.

LC-MS with Acidic Conditions

Apparatus: Agilent 1100 series with mass spectroscopy detection (MS: Finnigan single quadrupole). Column: Agilent Zorbax SB-Aq, (3.5 um, 4.6×50 mm). Conditions: MeCN [eluent A]; water+0.04% TFA [eluent B]. Gradient: 95% B→5% B over 1.5 min. (flow: 4.5 ml/min.). Detection: UV+MS.

1) Synthesis of 5-methoxy-2-(2H-1,2,3-triazol-2-yl)benzoic acid

2-Iodo-5-methoxy benzoic acid (15.0 g; 53.9 mmol) is dissolved in anhydrous DMF (45 ml) followed by the addition of 1H-1,2,3-triazole (7.452 g; 108 mmol) and cesium carbonate (35.155 g; 108 mmol). By the addition of cesium carbonate the temperature of the reaction mixture increases to 40° C. and gas evolved from the reaction mixture. Copper(I)iodide (514 mg; 2.7 mmol) is added. This triggers a strongly exothermic reaction and the temperature of the reaction mixture reaches 70° C. within a few seconds. Stirring is continued for 30 minutes. Then the DMF is evaporated under reduced pressure followed by the addition of water (170 ml) and EtOAc (90 ml). The mixture is vigorously stirred and by the addition of citric acid monohydrate the pH is adjusted to 3-4. The precipitate is filtered off and washed with water and EtOAc and discarded. The filtrate is poured into a separation funnel and the phases are separated. The water phase is extracted again with EtOAc. The combined organic layers are dried over MgSO$_4$, filtered and the solvent is evaporated to give 7.1 g of 5-methoxy-2-(2H-1,2,3-triazol-2-yl)benzoic acid as a white powder of 94% purity (6% impurity is the regioisomerically N1-linked triazolo-derivative); $t_R$ [min]=0.60; [M+H]$^+$=220.21.

2) Synthesis of (S)-1-(tert-butoxycarbonyl)-2-methylpyrrolidine-2-carboxylic acid 2-Methyl-L-proline hydrochloride (99.7 g; 602 mmol) is dissolved in a 1/1-mixture of MeCN and water (800 ml) and triethylamine (254 ml; 1810 mmol) is added. The temperature of the reaction mixture slightly rises. The reaction mixture is cooled to 10° C. to 15° C. followed by careful addition of a solution of Boc$_2$O (145 g; 662 mmol) in MeCN (200 ml) over 10 minutes. Stirring at RT is continued for 2 hours. The MeCN is evaporated under reduced pressure and aq. NaOH solution (2M; 250 ml) is added to the residual aq. part of the reaction mixture. The water layer is washed with Et$_2$O (2×300 ml) then cooled to 0° C. followed by slow and careful addition of aq. HCl (25%) to adjust the pH to 2. During this procedure a suspension forms. The precipitate is filtered off and dried at HV to give 110.9 g of the title compound as a beige powder; $t_R$ [min]=0.68; [M+H]$^+$=230.14.

3) Synthesis of (S)-tert-butyl 2-((2-amino-4-chloro-3-methylphenyl)carbamoyl)-2-methylpyrrolidine-1-carboxylate (S)-1-(tert-butoxycarbonyl)-2-methylpyrrolidine-2-carboxylic acid (60 g; 262 mmol) and HATU (100 g; 264 mmol) is suspended in DCM (600 ml) followed by the addition of DIPEA (84.6 g; 654 mmol) and 6-chloro-2,3-diaminotoluene (41 g; 262 mmol). The reaction mixture is stirred at rt for 14 hours then concentrated under reduced pressure and to the residue is added water followed by the extraction of the product with EtOAc (3×). The combined organic layers are washed with brine, dried over MgSO$_4$, filtered and the solvent is evaporated under reduced pressure to give 185 g of the title compound as a dark brownish oil, which is used in the next step without further purification; $t_R$ [min]=0.89; [M+H]$^+$=368.01.

4) Synthesis of (S)-tert-butyl 2-(5-chloro-4-methyl-1H-benzo[d]imidazol-2-yl)-2-methylpyrrolidine-1-carboxylate (S)-tert-butyl 2-((2-amino-4-chloro-3-methylphenyl)carbamoyl)-2-methylpyrrolidine-1-carboxylate (185 g; 427 mmol) are dissolved in AcOH (100%; 611 ml), heated to 100° C. and stirring continued for 90 minutes. The AcOH is evaporated under reduced pressure and the residue is dissolved in DCM followed by careful addition of saturated sodium bicarbonate solution. The phases are separated, the aq. phase is extracted once more with DCM, the combined aq. phases are dried over MgSO$_4$, filtered and the solvent is evaporated under reduced pressure to give 142.92 g of the title compound as a dark brown oil which is used in the next step without further purification; $t_R$ [min]=0.69; [M+H]$^+$=350.04.

5) Synthesis of (S)-5-chloro-4-methyl-2-(2-methyl-pyrrolidin-2-yl)-1H-benzo[d]imidazole hydrochloride (S)-tert-butyl 2-(5-chloro-4-methyl-1H-benzo[d]imidazol-2-yl)-2-methylpyrrolidine-1-carboxylate (355.53 g; 1.02 mol) are dissolved in dioxane (750 ml) followed by careful addition of HCl solution in dioxane (4M; 750 ml; 3.05 mol). The reaction mixture is stirred for 3 hours followed by the addition of Et$_2$O (800 ml) which triggered precipitation of the product. The solid is filtered off and dried at high vacuum to give 298.84 g of the title compound as a redish powder; $t_R$ [min]=0.59; [M+H]$^+$=250.23.

6) Synthesis of [(S)-2-(5-chloro-4-methyl-1H-benzoimidazol-2-yl)-2-methyl-pyrrolidin-1-yl]-(5-methoxy-2-[1,2,3]triazol-2-yl-phenyl)-methanone (S)-5-chloro-4-methyl-2-(2-methylpyrrolidin-2-yl)-1H-benzo[d]imidazole hydrochloride (62.8 g; 121 mmol) is dissolved in DCM (750 ml) followed by the addition of 5-methoxy-2-(2H-1,2,3-triazol-2-yl)benzoic acid (62.8 g; 121 mmol) and DIPEA (103 ml; 603 mmol). Stirring is continued for 10 minutes followed by the addition of HATU (47 g; 124 mmol). The reaction mixture is stirred for 16 hours at RT. The solvents are evaporated under reduced pressure and the residue is dissolved in EtOAc (1000 ml) and washed with water (3×750 ml). The organic phase is dried over MgSO$_4$, filtered and the solvent is evaporated under reduced pressure. The residue is purified by CC with EtOAc/hexane=2/1 to give 36.68 g of the title compound as an amorphous white powder. $t_R$ [min]=0.73; [M+H]$^+$=450.96. The title compound can be transferred to the corresponding hydrochloric acid salt using standard conditions such as isopropanol/HCl in isopropanol.

7) Synthesis of methyl 2-iodo-5-methylbenzoate

2-Iodo-5-methylbenzoic acid (101 g; 387 mmol) is dissolved in MeOH (700 ml) followed by the addition of concentrated sulfuric acid (97%; 10.4 ml; 193 mmol). The reaction mixture is heated to 83° C. for 16 hours, cooled again to RT followed by slow and careful addition of aq. 1M NaOH solution until pH 8 is reached. The MeOH is evaporated under reduced pressure and the remaining aq. phase is extracted with DCM (2×350 ml). The combined organic layers are washed with water (400 ml), dried over MgSO$_4$, filtered and the solvent is evaporated under reduced pressure to give 104.13 g of the title compound as a yellow liquid. $t_R$ [min]=0.89; [M+H]$^+$=not detected.

8) Synthesis of methyl 5-methyl-2-(4,4,5,5-tetramethyl-1,3,2-dioxaborolan-2-yl)benzoate Methyl 2-iodo-5-methylbenzoate (104.13 g; 358 mmol) is dissolved in THF (500 ml) under an inert nitrogen atmosphere followed by the addition of triethylamine (150 ml; 1.07 mol) and 4,4,5,5-tetramethyl-1,3,2-dioxaborolane (68.8 g; 537 mmol). The mixture is additionally degassed by bubbling nitrogen gas in for 5 min. Then tri-(o-tolyl)-phosphine (5.45 g; 17.9 mmol) and palladium(II)-acetate (2.01 g; 8.96 mmol) is added and the mixture is heated to 75° C. for 1 hour. The reaction mixture is cooled to 0° C. followed by careful addition of sat. aq. NH$_4$Cl solution (to the point where no further gas evolution occurs). The black suspension is filtered, the filtrate is concentrated under reduced pressure and water is added to the residue. The product is extracted with EtOAc (2×200 ml). The combined EtOAc layers are dried over MgSO$_4$, filtered and the solvent is evaporated under reduced pressure. The residue is purified by CC with heptane/EtOAc=95/5, to give 82.7 of the title compound as a slightly orange solid; $t_R$ [min]=0.92; [M+H]$^+$=277.22.

9) Synthesis of methyl 5-methyl-2-(pyrimidin-2-yl)benzoate

5-Methyl-2-(4,4,5,5-tetramethyl-1,3,2-dioxaborolan-2-yl)benzoate (165.45 g; 599 mmol) is dissolved in 2-methlytetrahydrofurane (900 ml). 2-Chloropyrimidine (82.3 g; 719 mmol), solid sodium carbonate (159 g, 1.5 mol) and water (275 ml) are added and the reaction mixture is degassed by bubbling nitrogen gas in for 5 minutes followed by the addition of [1,1'-bis(diphenylphosphino) ferrocene]dichloropalladium(II), complex with DCM (CAS: 95464-05-4; Pd(dppf)Cl2×DCM; 39.1 mg; 47.9 mmol). The reaction mixture is heated to 75° C. internal temperature for 40 hours, then cooled to RT, filtered and to the filtrate is added water followed by the extraction of the product with EtOAc (2×700 ml). The combined organic layers are dried over MgSO$_4$, filtered and the solvent is evaporated under reduced pressure. The residue is purified by CC with heptane/EtOAc=2/1 to give 86.13 g of the title compound as a slightly yellow solid; $t_R$ [min]=0.72; [M+H]$^+$=229.17.

10) Synthesis of 5-methyl-2-(pyrimidin-2-yl)benzoic acid

Methyl 5-methyl-2-(pyrimidin-2-yl)benzoate (86.1 g; 377 mmol) are dissolved in THF (350 ml) followed by the addition of water (350 ml) and aq. NaOH (190 ml; 4M). The reaction mixture is heated to 70° C. for 4 hours. The organic solvent is distilled off under reduced pressure and the aq. phase is extracted with DCM. Then the aq. phase is cooled to 0° C. and the pH is adjusted to pH=1 by careful addition of aq. 2M hydrochloric acid solution which results in the formation of a suspension. The solid is filtered off and dried at high vacuum to give 59.98 g of the title compound as a beige solid; $t_R$ [min]=0.58; [M+H]$^+$=215.14.

11) Synthesis of (S)-tert-butyl 2-((2-amino-5-bromo-3-methylphenyl)carbamoyl)-2-methylpyrrolidine-1-carboxylate (S)-1-(tert-butoxycarbonyl)-2-methylpyrrolidine-2-carboxylic acid (2.5 g; 10.9 mmol) is dissolved in DCM (25 ml) and HATU (4.2 g; 11 mmol) is added. To this mixture DIPEA (5.6 ml, 32.7 mmol) and 5-bromo-3-methylbenzene-1,2-diamine is added. The reaction mixture is stirred at RT for 16 hours. The solvents are evaporated under reduced pressure and the residue is dissolved in EtOAc (200 ml) and washed with water (3×150 ml). The organic layer is dried over MgSO$_4$, filtered and the solvent is evaporated under reduced pressure. The residue is dried at high vacuum to give 5 g of the title compound; $t_R$ [min]=0.90; [M+H]$^+$=414.25.

12) Synthesis of (S)-tert-butyl 2-(5-bromo-7-methyl-1H-benzo[d]imidazol-2-yl)-2-methylpyrrolidine-1-carboxylate (S)-tert-butyl 2-((2-amino-5-bromo-3-methylphenyl)carbamoyl)-2-methylpyrrolidine-1-carboxylate (4.97 g; 12.1 mmol) are dissolved in AcOH (100%; 41 ml) and the mixture is heated to 100° C. and stirring is continued for 1 h. The AcOH is evaporated under reduced pressure and to the residue is slowly and carefully added sat. aq. NaHCO$_3$ solution (250 ml). The product is extracted with EtOAc (2×250 ml). The combined organic layers are dried over MgSO$_4$, filtered and the solvent is evaporated under reduced pressure. The residue is dried at high vacuum to give 4.3 g of the title compound; $t_R$ [min]=0.71; [M+H]$^+$=394.27.

13) Synthesis of (S)-5-bromo-7-methyl-2-(2-methylpyrrolidin-2-yl)-1H-benzo[d]imidazole hydrochloride (S)-tert-butyl 2-(5-bromo-7-methyl-1H-benzo[d]imidazol-2-yl)-2-methylpyrrolidine-1-carboxylate (4.26 g; 10.8 mmol) are dissolved in dioxane (31 ml) and a solution of hydrochloric acid in dioxane (4M; 31 ml; 130 mmol) is added followed by the addition of MeOH (5 ml). Stirring is continued for 2 hours followed by the addition of Et$_2$O (250 ml) which leads to the precipitation of a white powder which is filtered off and is washed with Et$_2$O (25 ml). The brownish powder is dissolved in MeOH (50 ml) and 1 g of activated charcoal (Norit) is added and stirring is continued for 5 minutes then the charcoal is filtered off over celite and the solvent is evaporated under reduced pressure and the residue is dried at high vacuum to give 3.9 g of the title compound as a slightly reddish powder; $t_R$ [min]=0.61; [M+H]$^+$=294.09.

14) Synthesis of [(S)-2-(5-Bromo-7-methyl-1H-benzoimidazol-2-yl)-2-methyl-pyrrolidin-1-yl]-(5-methyl-2-pyrimidin-2-yl-phenyl)-methanone 5-Methyl-2-(pyrimidin-2-yl)benzoic acid (1.47 g; 6.86 mmol) is dissolved in DCM (50 ml) and dimethylaminopyridine (168 mg, 1.37 mmol) and EDC (1.45 g; 7.55 mmol) are added. Stirring is continued for 30 minutes followed by the addition of (S)-5-bromo-7-methyl-2-(2-methylpyrrolidin-2-yl)-1H-benzo[d]imidazole hydrochloride (2.27 g; 6.86 mmol). Stirring at RT is continued for 16 hours. Ethylacetate (150 ml) and sat. sodium hydrogencarbonate solution (100 ml) are added to the reaction mixture. The phases are separated and the aq. phase is extracted with EtOAc (50 ml). The combined organic layers are dried with MgSO$_4$, filtered and the solvent is evaporated under reduced pressure. The product is purified by preparative HPLC (conditions C) to give 2.07 g of the title compound as a white powder; $t_R$ [min]=0.73; [M+H]$^+$=492.14.

In analogy to the procedures described herein before, the following examples are prepared.

TABLE 1

| Example | Compound name. LC-MS data |
|---|---|
| 1 | (5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.83; [M + H]$^+$ = 455.3 |
| 2 | [(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.82; [M + H]$^+$ = 479.2 |
| 3 | (5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone. LC-MS: $t_R$ = 0.82; [M + H]$^+$ = 471.2 |
| 4 | [(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.68; [M + H]$^+$ = 447.4 |
| 5 | [(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.82; [M + H]$^+$ = 483.2 |
| 6 | [(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 1.01; [M + H]$^+$ = 489.2 |
| 7 | [(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone. LC-MS: $t_R$ = 0.78; [M + H]$^+$ = 451.3 |
| 8 | [(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone. LC-MS: $t_R$ = 0.64; [M + H]$^+$ = 463.3 |
| 9 | [(S)-2-(5,6-Dimethoxy-1H-benzoimidazol-2-yl)-2-methyl-pyrrolidin-1-yl]-(5-methyl-2-pyrazol-1-yl-phenyl)-methanone. LC-MS: $t_R$ = 0.67; [M + H]$^+$ = 446.3 |
| 10 | [(S)-2-(5-Chloro-4-methyl-1H-benzoimidazol-2-yl)-2-methyl-pyrrolidin-1-yl]-(5-methyl-2-pyrimidin-2-yl-phenyl)-methanone. LC-MS: $t_R$ = 77; [M + H]$^+$ = 446.2 |
| 11 | [(S)-2-(5-Bromo-7-methyl-1H-benzoimidazol-2-yl)-2-methyl-pyrrolidin-1-yl]-(5-methyl-2-pyrimidin-2-yl-phenyl)-methanone. LC-MS: $t_R$ = 0.84; [M + H]$^+$ = 490.3 |

II—Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% CO$_2$.

Human orexin-A as an agonist is prepared as 1 mM stock solution in MeOH: water (1:1), diluted in HBSS containing 0.1% bovine serum albumin (BSA), NaHCO$_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), NaHCO$_3$: 0.375 g/l and 20 mM HEPES. On the day of the assay, 50 µl of staining buffer (HBSS containing 1% FCS, 20 mM HEPES, NaHCO$_3$: 0.375 g/l, 5 mM probenecid (Sigma) and 3 μM of the fluorescent calcium indicator fluo-4 AM (1 mM stock solution in DMSO, containing 10% pluronic) is added to each well. The 384-well cell-plates are incubated for 50 min at 37° C. in 5% CO$_2$ followed by equilibration at RT for 30 min before measurement.

Within the Fluorescent Imaging Plate Reader (FLIPR Tetra, Molecular Devices), antagonists are added to the plate in a volume of 10 μl/well, incubated for 120 min and finally 10 μl/well of agonist is added. Fluorescence is measured for each well at 1 second intervals, and the height of each fluorescence peak is compared to the height of the fluorescence peak induced by an approximate EC$_{70}$ (for example 5 nM) of orexin-A with vehicle in place of antagonist. The IC$_{50}$ value (the concentration of compound needed to inhibit 50% of the agonistic response) is determined and may be normalized using the obtained IC$_{50}$ value of a on-plate reference compound. Optimized conditions are achieved by adjustment of pipetting speed and cell splitting regime. The calculated IC$_{50}$ values may fluctuate depending on the daily cellular assay performance. Fluctuations of this kind are known to those skilled in the art. Average IC$_{50}$ values from several measurements are given as mean values.

Antagonistic activities of example compounds with respect to the Ox$_1$ and the Ox$_2$ receptor are displayed in Table 2.

diminished ATP metabolism) may lead to upregulated (hypersensitized) adenosine receptors.

Protocols for Agitation Induced by Caffeine in Rats and Dogs:

Electroencephalography (EEG) and Electromyography (EMG) signals were measured by telemetry using radiotelemetric implants (Data Science Int.).

(1) In rats (nocturnal species): The compound of Ex. 7, the compound of Ex 11 and caffeine were dosed p.o. by gavage at the indicated dose and time point.

Conditions are as follows: Lights off at 11 am, drug or vehicle at 4:30 pm, caffeine or vehicle at 5 pm, lights on at 11 pm, online continuous radiotelemetric recording of EEG, EMG, thermoregulation and locomotor activity over several circadian cycles. The attenuating effects of orexin receptor antagonists are quantified for potency, efficacy, onset of effects on electrophysiological markers.

FIG. 1 show the activity (counts per minute, n=8 animals) over time (the grey zone representing the night active period). Dosing of drug or vehicle is indicated at (1), 30 minutes before dosing of caffeine or vehicle, indicated at (2). Curves show: (A): vehicle at (1) and vehicle at (2); (B): compound of Ex. 7—HCl salt (108 mg/kg p.o.) at (1) and vehicle at (2); (C): vehicle at (1) and caffeine at (2); and (D): compound of Ex. 7—HCl salt (108 mg/kg p.o.) at (1) and caffeine at (2).

Figure 2:
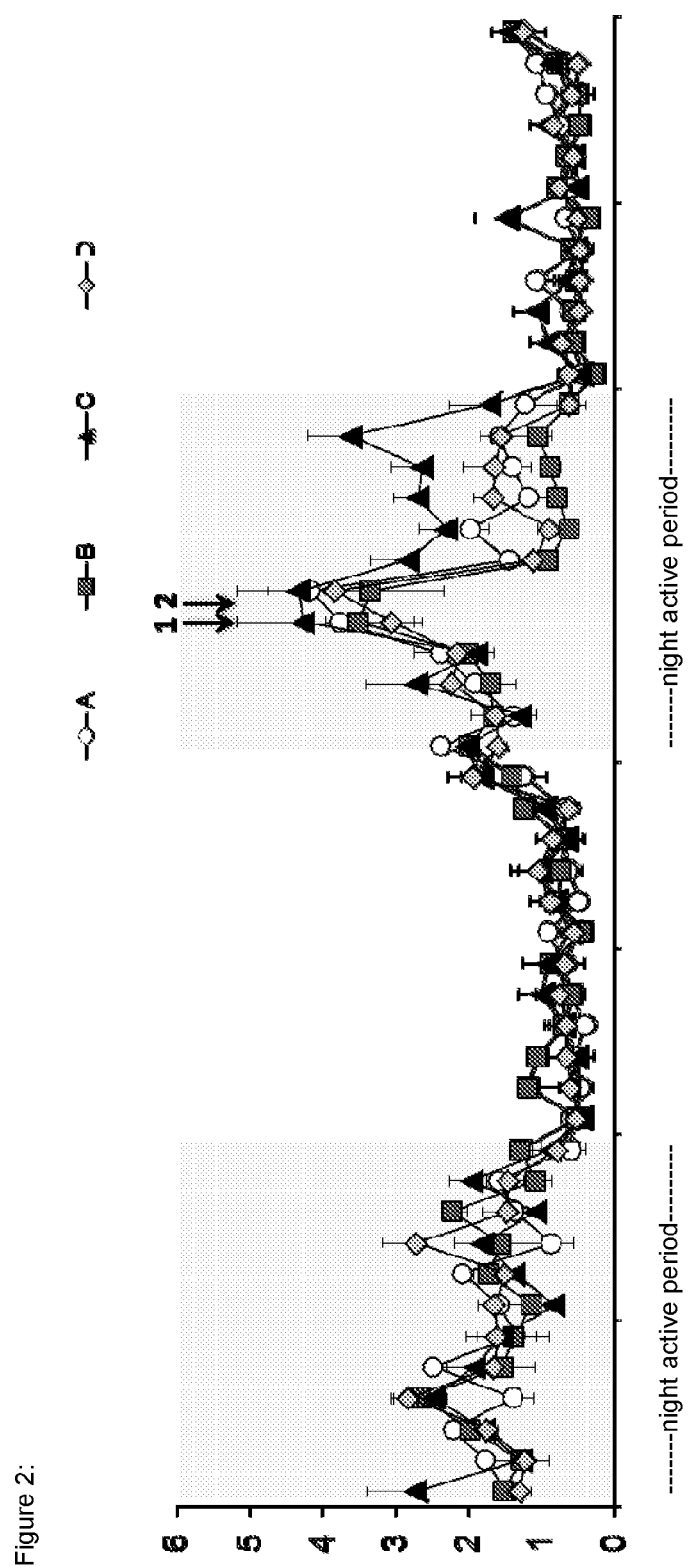
FIG. 2 shows the effect of the compound of example 11 in a coffein-induced agitation model in the rat.

FIG. 2 show activity (count per minute, n=8 animals) over time (the grey zone representing the night active period).

TABLE 2

| Example Number | IC$_{50}$ Ox1 [nM] | IC$_{50}$ Ox2 [nM] | Example Number | IC$_{50}$ Ox1 [nM] | IC$_{50}$ Ox2 [nM] | Example Number | IC$_{50}$ Ox1 [nM] | IC$_{50}$ Ox2 [nM] |
|---|---|---|---|---|---|---|---|---|
| Ex. 1 | 8 | 81 | Ex. 2 | 9 | 20 | Ex. 3 | 19 | 161 |
| Ex. 4 | 22 | 18 | Ex. 5 | 15 | 80 | Ex. 6 | 2 | 9 |
| Ex. 7 | 2 | 3 | Ex. 8 | 27 | 23 | Ex. 9 | 27 | 15 |
| Ex. 10 | 2 | 4 | Ex. 11 | 6 | 21 | | | |

Effect of Exemplified Compounds on Agitation Induced by Caffeine in Rats and Dogs Neurobiological and Neuropharmacological Rationales:

Caffeine is used as a tool to simulate deficient inhibitory VLPO-SCN input to hypothalamic orexin neurons. Adenosine receptors (mainly adenosine A1 and A2A receptors) negatively regulate the firing of orexin neurons that mediate wakefulness by reinforcing the ascending arousal monoaminergic medio-cortical system. Throughout the day, endogenous adenosine builds up from ATP metabolism and gradually contributes, with Gaba and melatonin, to increase sleep pressure through VLPO-mediated inhibition of midbrain orexin and monoamine neurons. Caffeine, an adenosine A1 and A2A receptor antagonist, blocks adenosinergic inhibition on orexin neurons, thereby reinforcing orexinergic activation and increasing alertness. This essentially represents one of the neurobiological mechanism of caffeine's alerting and awakening properties Late day acute oral caffeine (in diurnal species) is used to experimentally simulate VLPO and SCN deafferentation leading to sundown agitation; this has elicited orexinergic activation and increased alertness. High dose caffeine is typically needed to induce agitation and hyperalertness in healthy animals with normal adenosine tone and receptors.

Caffeine consumption is contraindicated in elderly patients suffering from sundown syndrome. Caffeinated beverages are suspected to exacerbate agitation symptoms in sundown syndrome patients. VLPO and SCN deafferentation as well as low endogenous adenosine tone (due to Dosing of drug or vehicle is indicated at (1), 30 minutes before dosing of caffeine or vehicle indicated at (2). Curves show: (A): vehicle at (1) and vehicle at (2); (B): compound of Ex. 11 (100 mg/kg p.o.) at (1) and vehicle at (2); (C): vehicle at (1) and caffeine at (2); and (D): compound of Ex. 11 (100 mg/kg p.o.) at (1) and caffeine at (2).

(2) In dogs (diurnal species): The compound of Ex. 7 and caffeine were dosed p.o. by gavage at the indicated dose and time point.

Conditions are as follows: Lights on at 7 am, drug or vehicle at 1:30 pm, caffeine or vehicle at 2 pm, lights off at 7 pm, online 24 h radiotelemetric recording (10 am-10 am) of EEG, EMG, thermoregulation and locomotor activity. The effects of the tested compound are quantified for potency, efficacy, onset and duration of effects on canine electrophysiological and clinical markers of caffeine agitation and hyperalertness.

Figure 3:
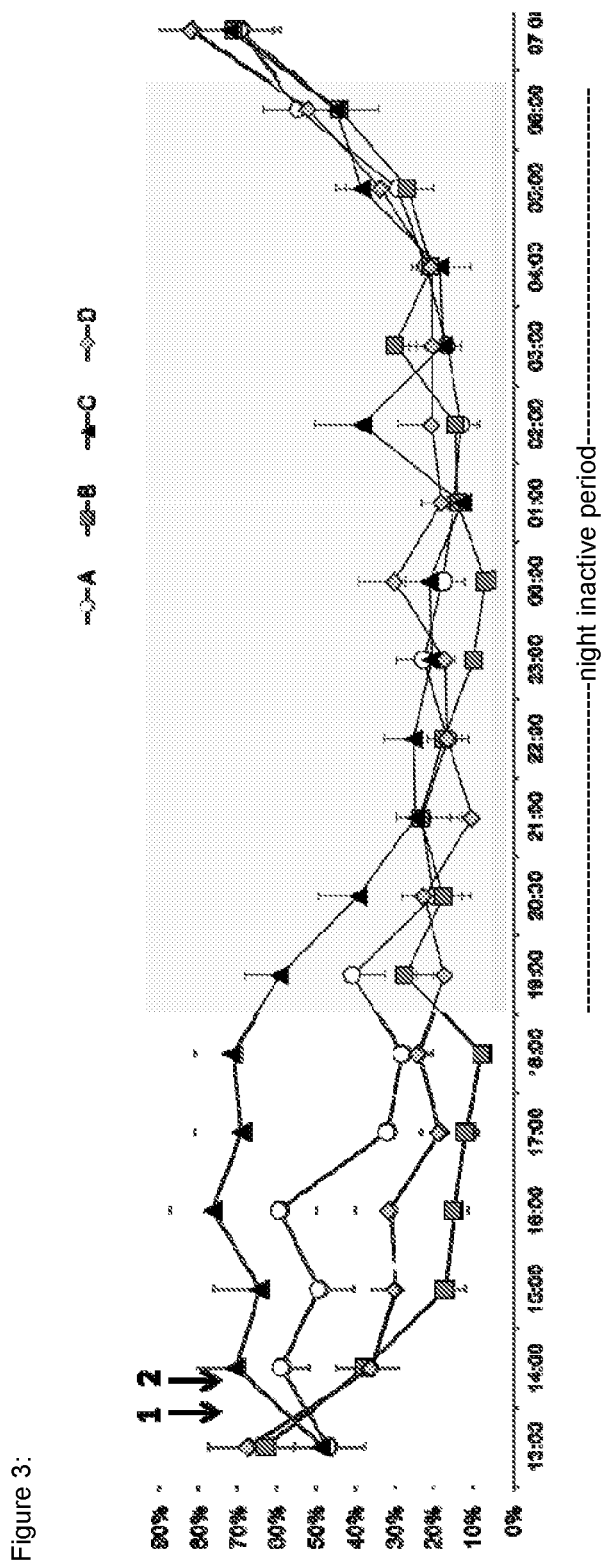
FIG. 3 shows the effect of the compound of example 7 in a coffein-induced agitation model in the dog.

FIG. 3 show the time spent in active wake (% of total time, n=8 animals) over time (from 1 pm to 7 am, grey zone representing the night inactive period from 7 pm to 7 am). Dosing of drug or vehicle is indicated at (1), 30 minutes before dosing of caffeine or vehicle indicated at (2). Curves show: (A): vehicle at (1) and vehicle at (2); (B): compound of Ex. 7 (90 mg/dog) at (1) and vehicle at (2); (C): vehicle at (1) and caffeine at (2); and (D): compound of Ex. 7 (90 mg/dog) at (1) and caffeine at (2).

The invention claimed is:

1. A method of treatment of sundown syndrome, comprising administering to a patient in need thereof a compound of the formula (I):

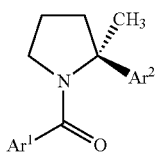

Formula (I)

in free or pharmaceutically acceptable salt form,
wherein the compound of formula (I) is in absolute configuration (S);
Ar¹ represents

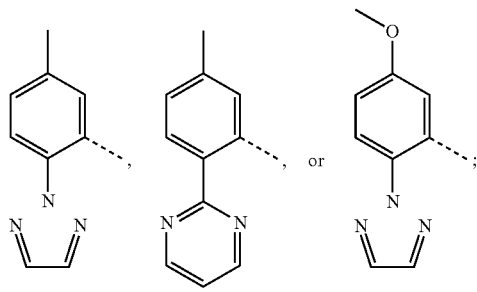

and Ar² represents

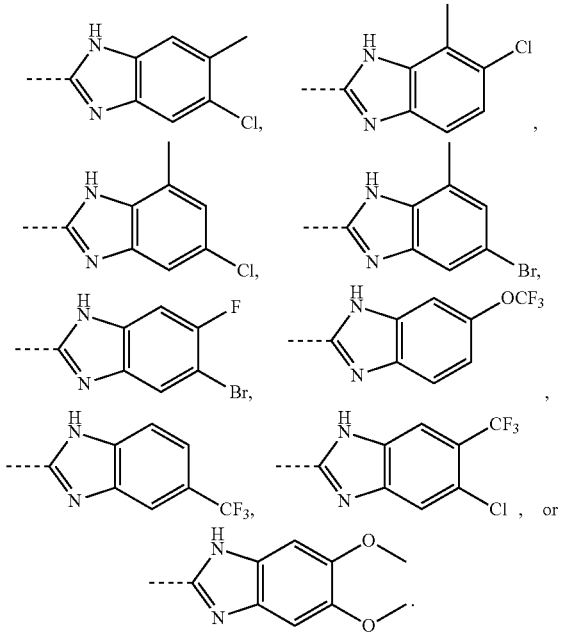

2. The method according to claim 1, wherein the compound is:
[(S)-2-(5-Chloro-4-methyl-1H-benzoimidazol-2-yl)-2-methyl-pyrrolidin-1-yl]-(5-methyl-2-pyrimidin-2-yl-phenyl)-methanone;
[(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone;
[(S)-2-(5-Bromo-7-methyl-1H-benzoimidazol-2-yl)-2-methyl-pyrrolidin-1-yl]-(5-methyl-2-pyrimidin-2-yl-phenyl)-methanone;
[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone;
[(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone;
[(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone;
[(S)-2-(5,6-Dimethoxy-1H-benzoimidazol-2-yl)-2-methyl-pyrrolidin-1-yl]-(5-methyl-2-pyrazol-1-yl-phenyl)-methanone;
[(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone;
[(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone;
(5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone; or
(5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone,
in free or pharmaceutically acceptable salt form.

3. The method according to claim 1, wherein the compound is:
[(S)-2-(5-Bromo-7-methyl-1H-benzoimidazol-2-yl)-2-methyl-pyrrolidin-1-yl]-(5-methyl-2-pyrimidin-2-yl-phenyl)-methanone,
in free or pharmaceutically acceptable salt form.

4. The method according to claim 1, wherein the compound is:
[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone,
in free or pharmaceutically acceptable salt form.

5. The method according to claim 1, wherein said patient has a dementia of Alzheimer's type.

6. The method of claim 5, wherein the patient has middle stage Alzheimer dementia.

7. The method of claim 5, wherein the sundown syndrome is afternoon sundown syndrome.

8. The method according to claim 4, wherein said patient has a dementia of Alzheimer's type.

9. The method of claim 8, wherein the patient has middle stage Alzheimer dementia.

10. The method of claim 8, wherein the sundown syndrome is afternoon sundown syndrome.

11. The method of claim 4, wherein what is treated is increased agitation.

12. The method of claim 8, wherein what is treated is increased agitation.

13. The method of claim 9, wherein what is treated is increased agitation.

14. The method of claim 10, wherein what is treated is increased agitation.

* * * * *